United States Patent [19]

Elkow

[11] 4,378,014
[45] Mar. 29, 1983

[54] APPARATUS FOR AND METHOD OF ADMINISTERING INTRAVENOUS FLUID

[76] Inventor: Robert D. Elkow, 8 Silver La., St. Louis, Mo. 63122

[21] Appl. No.: 248,432

[22] Filed: Mar. 27, 1981

[51] Int. Cl.$^3$ .............................................. A61M 5/00
[52] U.S. Cl. ................................ 128/214 E; 340/614; 340/668
[58] Field of Search ........... 128/214, 214 E, DIG. 13; 340/604, 605, 614, 665, 668

[56] References Cited

U.S. PATENT DOCUMENTS 3,992,706 11/1976 Tunney et al. ................... 128/214 E
4,014,010 3/1977 Jinotti .............................. 128/214 C
4,275,726 6/1981 Schael ............................. 128/214 E

OTHER PUBLICATIONS

Excerpt from Article in Journal of Thoracic and Cardiovascular Surgery, vol. 40, No. 4, Entitled "Autogenous Oxygenation with Cardiac Bypass, Hypothermia, and Ventricular Clamp," pp. 536–548.

Primary Examiner—Stephen C. Pellegrino
Attorney, Agent, or Firm—Polster, Polster & Lucchesi

[57] ABSTRACT

Apparatus is disclosed for monitoring the administering of an intravenous fluid to a patient from a flexible wall container (e.g., a plastic bag) and for generating a signal upon the level of the fluid in the I.V. bag reaching a predetermined level. The walls of the bag are flexible and are spaced apart when the bag is full and move toward one another as the fluid is discharged from the bag and as the level of the fluid in the bag drops. The apparatus includes a frame which may be removably secured on the exterior of the bag at any predetermined location (level) on the bag. The apparatus includes a signal generator (e.g., an alarm) which is movable with the frame as the fluid level drops within the bag and as the bag sidwalls move toward one another from an open position in which the signal generator is de-energized to a closed position in which a signal is generated to sound an alarm or to otherwise indicate that the level of the fluid remaining in the bag has been reduced to a predetermined level.

A method of monitoring the fluid level in an I.V. bag is also disclosed.

13 Claims, 9 Drawing Figures

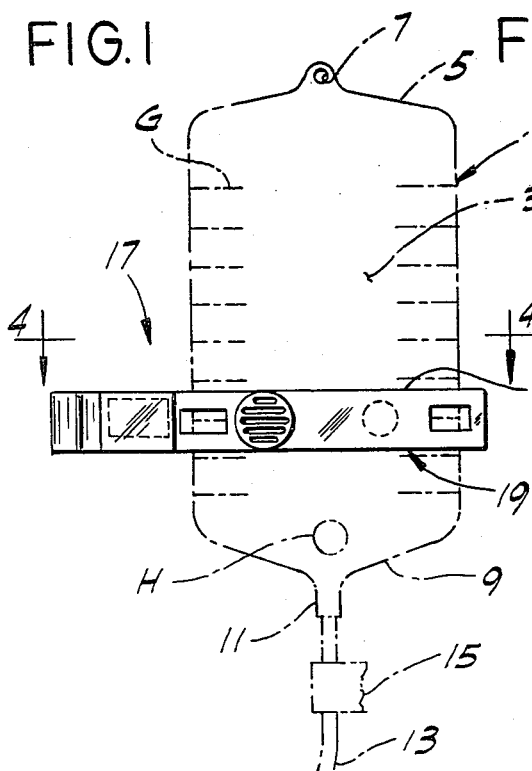
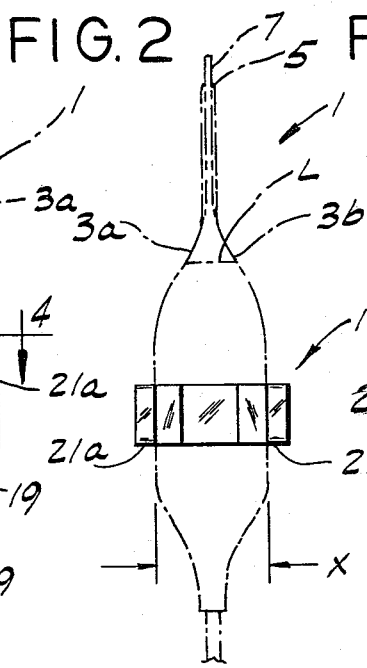
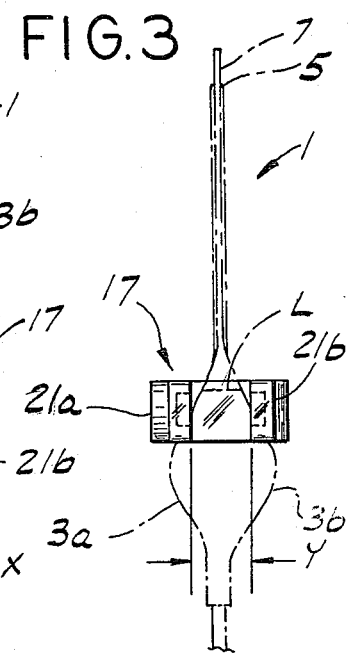
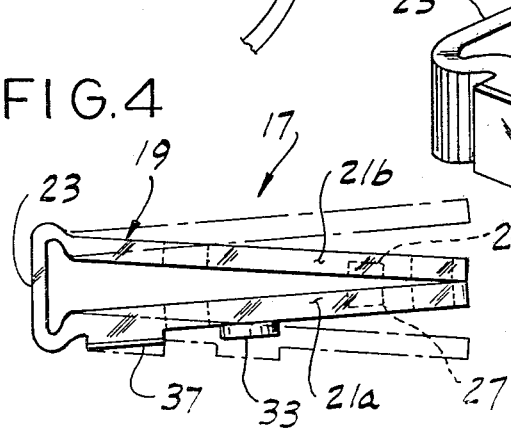
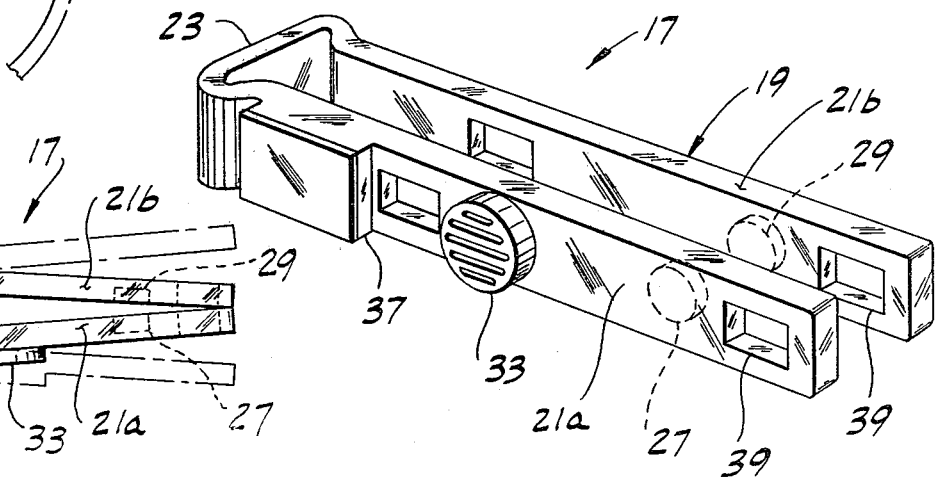
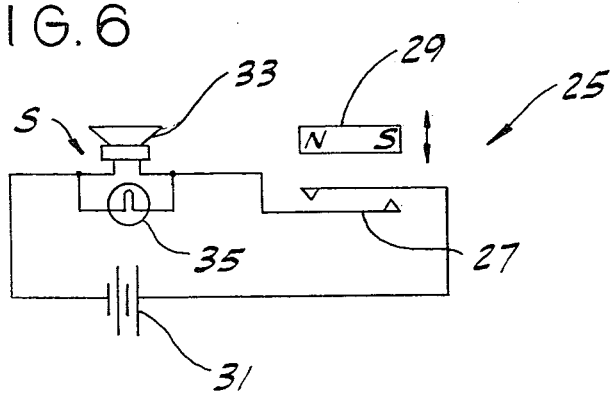

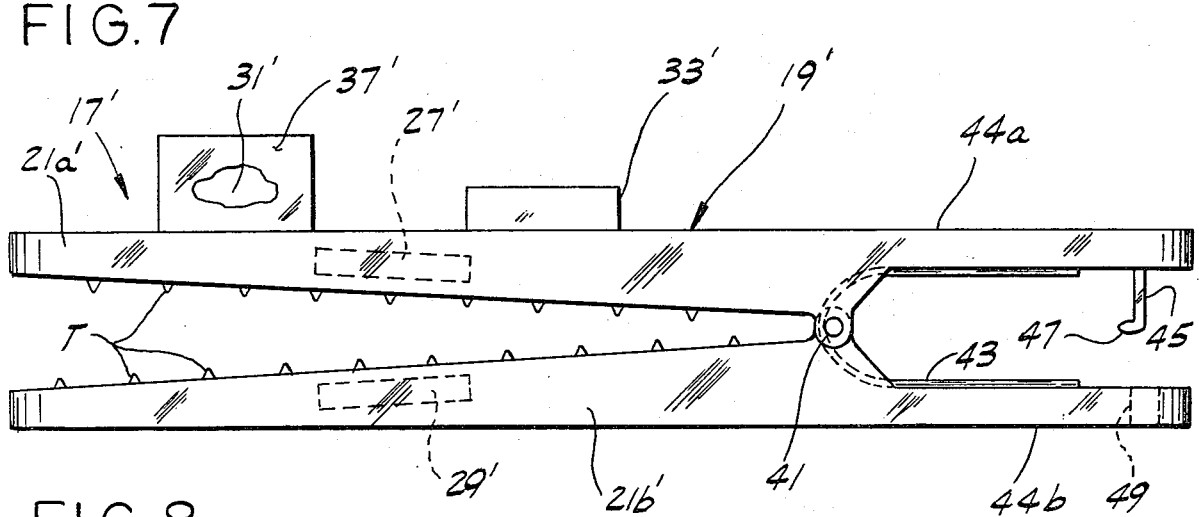
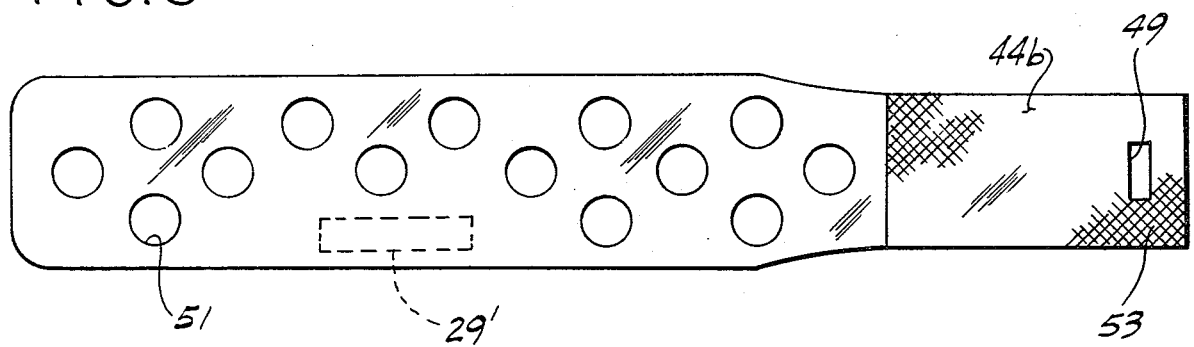
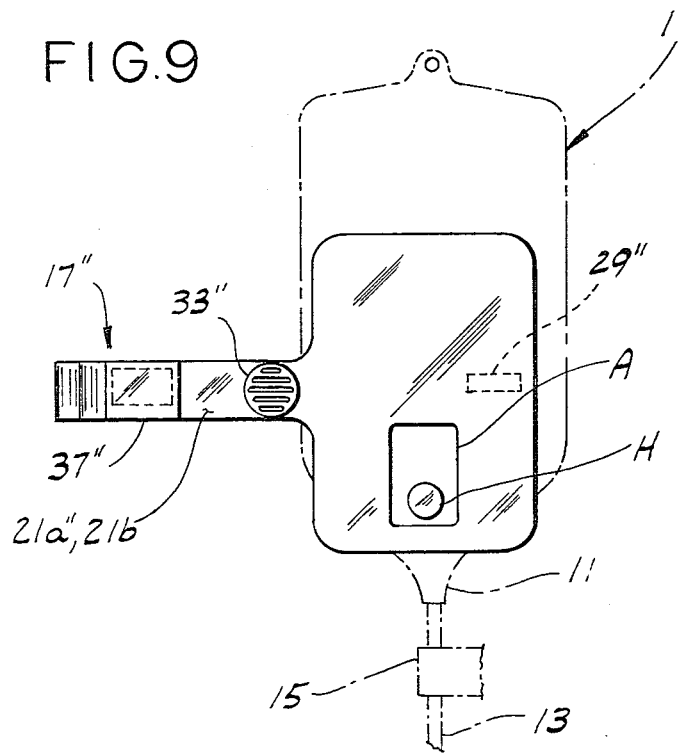

APPARATUS FOR AND METHOD OF ADMINISTERING INTRAVENOUS FLUID

BACKGROUND OF THE INVENTION

This invention relates to a system of monitoring the level of fluid remaining in a collapsible wall, intravenous (I.V.) bag so as to sound an alarm or to otherwise alert hospital personnel that the level of fluid remaining in the I.V. bag has decreased to a predetermined level.

In the treatment of many hospital patients, it is conventional to administer fluids and medication intravenously. Intravenous fluid is administered by inserting a needle or catheter into a vein of the patient (e.g., in the proximal forearm). Once the catheter is in place in a vein, it is typically taped or otherwise secured to the patient and is connected by means of flexible rubber or plastic tubing to a supply of liquid to be fed through the tubing and to be admixed with the blood flowing through the vein. Typically, the intravenous fluid supply is elevated on an I.V. pole or the like adjacent the patient's bed, wheelchair, stretcher, or may be carried by an ambulatory patient so that it has a sufficient hydrostatic pressure to overcome the pressure of the blood flowing through the vein. Typically, the I.V. container and tubing is equipped with a drip indicator and valve so that the rate at which the I.V. fluid is administered can be accurately regulated.

In recent years, the use of flexible wall bags has, for the most part, replaced glass or other rigid bottles as the containers for I.V. solutions. I.V. bags may come in a variety of volumes (e.g., 250 ml, 500 ml, 1 liter etc.) the I.V. bags are typically filled with a sterile liquid solution, such as a 5% dextrose and water solution, and have a sealed outlet into which a sterile probe connected to the tubing leading to the catheter implanted in the patient's vein may be inserted thereby to puncture the bag seal and to permit the I.V. solution to drain from the bag.

Oftentimes the flow rates for the I.V. solution or fluid is established by the treating physician such that a one liter bag may require many hours to be administered to the patient. Also, it is conventional to administer medication by injecting the medication into the bag by means of a hypodermic needle inserted through a puncturable seal provided in the bag wherein the medication is administered simultaneously with the I.V. solution. Oftentimes, the treating physician may direct that the medication by administered only after the patient has received a predetermined quantity of the I.V. solution. I.V. fluids are, of course, also used to increase a patient's fluid level in various treatment procedures, such as in administering plasma or whole blood, or in conducting fluid challenge tests.

In the event the I.V. solution is totally drained from the bag, blood backs up into the catheter and at least partially into the tubing connected to the catheter. This will result in clotting of the blood, other medical complications and, in psychological concerns to the patient. Thus, it is imperative for nurses to keep a regular and careful check to insure that a sufficient quantity of the I.V. solution remains in the bag.

However, nurses sometimes needlessly change the bag when ample quantities of the I.V. fluid remain in the bag and this results in waste of the remaining I.V. solution and in additional expense to the patient. Also, the patient may not get the full dosage of medication contained in the I.V. solution. Thus, nursing personnel must keep a vigilant check on the level of and flow rate of the I.V. solution.

Still further, patients may, during their sleep, dislodge the catheter from their vein or may pull the plastic tubing loose from the hub of the catheter thereby permitting the catheter to run dry and permitting the I.V. solution to rapidly drain from the bag, and/or to result in bleeding of the patient.

Because of the pain resulting from the insertion of an I.V. needle or catheter, hospital patients worry about the administration of I.V. solutions and whether the nursing staff will promptly change the I.V. bags when required.

I.V. infusion systems are currently available which continuously and positively control the administration of I.V. fluid to the patient. These prior I.V. infusion or monitoring systems are complicated. Typically, these I.V. infusion systems or monitors may either operate on the principle of counting the drops of I.V. solution discharged from the bag falling through the drip chamber of the drip meter provided in the tubing. Other I.V. administering and monitoring systems utilize a positive displacement pump operable at a very low, selectable flow rates to insure the administering of the fluid at a desired rate. However, all of the known I.V. infusion or monitoring systems are complex, complicated, and quite expensive. They all require an outside source of electrical power and they may present unnecessary electrical shock hazards to the patient. Of course, these systems may be useless in cases of power outages, or in large scale disasters (e.g., earthquakes) where no power source is available, or in forward battles in military combat. In many instances, only acute care hospital patients justify the expense of such sophisticated and complicated I.V. infusion or monitoring systems.

Still further, under present hospital economic and staffing constraints, registered nurses are responsible for a maximum number of patients. During busy periods, such as when several nurses are administering to a patient whose condition is deteriorating, other patients on the floor may not receive their full share of routine nursing functions, such as the monitoring of I.V. solutions. Because of the serious consequences which can result from an I.V. bag running dry or from the tubing becoming dislodged, increased pressures are imposed on nurses who are already working under stress at a high level of concentration and efficiency.

SUMMARY OF THE INVENTION

Among the many objects and features of this invention may be noted the provision of apparatus for monitoring the administering of intravenous fluid which may be readily applied to the exterior of an I.V. bag at any position on the bag so as to indicate when a predetermined quantity of the I.V. solution has been infused into the patient or when a predetermined level remains in the bag;

The provision of such an I.V. monitoring apparatus which may be readily used with I.V. bags of varying size and configurations;

The provision of such an I.V. monitoring apparatus which does not interfere with or does not contaminate the aseptic or sterile condition of the I.V. solution in the I.V. bag;

The provision of such an I.V. monitoring apparatus which is safe to use and which eliminates the possibility of electrical shock hazard and which requires no external source of electrical power and which thus may be used in remote locations;

The provision of such an I.V. monitoring apparatus which is self-contained, which is of simple and rugged construction, and, which in one embodiment, needs no external wiring or other connections;

The provision of such an I.V. monitoring apparatus which may be readily placed on the I.V. bag at one location thereof so as to indicate when a first quantity of I.V. solution has been administered to the patient and then moved to another location on the bag so as to indicate when a second quantity of I.V. solution has been administered;

The provision of such an I.V. monitoring apparatus which eliminates all spark hazard and may be used in oxygen therapy or in conjunction with possibly flammable gases, such as may be present in a surgical operating room;

The provision of a method of monitoring the administration of an I.V. solution in which an alarm or another signal is generated in response to the level of the I.V. solution in the bag reaching a predetermined level; and The provision of such an I.V. monitoring apparatus which is of simple and rugged construction and which is economical to manufacture and to use.

Other objects and features of this invention will be in part apparent and in part pointed out hereinafter.

Briefly stated, apparatus of this invention for monitoring the administering of an intravenous fluid to a patient from a flexible wall, collapsible container (e.g., a bag) and for generating a signal in response to the level of the fluid in the bag reaching a predetermined level is disclosed. The container has an outlet for the I.V. fluid and flexible sidewalls which are spaced apart when the bag is full and which move toward one another as the fluid is discharged from the bag and as the bag walls collapse toward one another. The apparatus comprises the frame adapted to be removably placed on the exterior of the bag at a preselected location or level. The apparatus includes means for generating a signal in response to the fluid remaining in the bag reaching the above-noted predetermined level with the signal generating means being movable with the frame as the fluid is discharged from the bag and as the bag sidewalls move toward one another from an open position in which the signal generating means is de-energized to a closed or actuated position in which the signal generating means is actuated to send a signal indicating that the fluid remaining in the bag has reached the above-noted predetermined level.

The method of this invention involves resiliently clipping or otherwise removably securing a sensing unit and a actuating unit to the exterior of an I.V. bag on opposite sides thereof. The sensing unit and the actuating unit constitute part of a signal generating means and are initially spaced apart a relatively far distance when the bag is full. As the bag empties, the sidewalls of the bag move together and upon the actuating unit and the sensing unit coming into relatively close proximity to one another, a signal is generated thereby indicating that the level of I.V. fluid remaining in the bag has reached a predetermined level. A signal is generated in response to this event occurring which may be utilized to alert nursing personnel or the like.

Other objects and features of this invention will be in part apparent and in part pointed out hereinafter.

BRIEF DESCRIPTION OF THE DRAWINGS

FIG. 1 is a front elevational view of a intravenous (I.V.) flexible wall bag (shown in phantom) hung in a vertical position from its top with a discharge opening at its bottom and showing a length of tubing leading from the bag to the patient, and further illustrating (in solid lines) a first embodiment of an I.V. monitoring apparatus or device of the present invention removably secured on the exterior of the I.V. bag at a desired location on the bag thereby to indicate when the level of the I.V. fluid in the bag reaches a predetermined level;

FIG. 2 is a right side elevational view of the I.V. bag and monitoring apparatus shown in FIG. 1 with the bag (shown in phantom) being substantially full of the I.V. solution and with the sidewalls of the bag (at the level of the monitoring apparatus) being spaced apart a distance X;

FIG. 3 is a view similar to FIG. 2 showing the I.V. bag with a greater quantity of the I.V. fluid discharged therefrom and with the sidewalls of the bag adjacent the monitoring apparatus moved closer together, as indicated by dimension Y, thereby to activate the monitoring device and to issue a signal indicating that the level of the I.V. fluid in the bag remaining has reached a predetermined level;

FIG. 4 is a top plan view of the I.V. monitoring apparatus shown in FIG. 1 taken along line 4—4 of FIG. 1 illustrating in solid lines a closed position for the various sides of the frame in which position the monitoring apparatus generates a signal indicating that the level of the I.V. fluid in the bag has reached a predetermined level and further illustrating (in phantom) an open position in which the apparatus may be resiliently applied to the exterior of a full I.V. bag, as illustrated in FIG. 2.;

FIG. 5 is a perspective view of the monitoring apparatus of the present invention shown in enlarged scale;

FIG. 6 is an electrical schematic of one embodiment of the signal generating means incorporated in the monitoring apparatus of the present invention;

FIG. 7 is a top plan view, similar to FIG. 4, (on an enlarged scale) of another embodiment of the monitoring apparatus of the present invention;

FIG. 8 is a front elevational view of the monitoring apparatus shown in FIG. 7; and FIG. 9 is a view similar to FIG. 1 illustrating still another embodiment of the device particularly adapted to accommodate the hub of an I.V. bag when the device is positioned on the bag proximate the hub.

Corresponding reference characters indicate corresponding parts throughout the several views of the drawings.

DESCRIPTION OF PREFERRED EMBODIMENTS

Referring now to the drawings, and particularly to FIGS. 1-6, an intravenous (I.V.) container or bag is indicated in its entirety by reference character 1. In FIGS. 1-3, the bag is shown to be illustrated in phantom. As typical, I.V. bag 1 is made of flexible, sheet synthetic resin material, preferably a waterproof, sterilizable material of plastic film. The bag has a pair opposed sidewalls 3a, 3b and the top of the bag, as indicated at 5, is sealed and has an eye 7 therethrough for hanging the bag in the position shown in FIGS. 1-3. The bag has a lower end 9 which is sealed closed with a puncturable outlet 11. As is typical, the bag is prefilled with a sterile, intravenous liquid solution and outlet 11 is sealed. In this manner the I.V. solution contained in the bag is maintained in a sterile condition until ready for use. As is typical, the bag is hung from eye 7 from an I.V. pole or the like adjacent the patient with the outlet 9 at the bottom and a length of flexible tubing 13 attached to the outlet 11 by puncturing the seal so as to permit the I.V. fluid within the bag to be discharged from the bag via the tubing. A hub H at the lower end of the bag is provided through which medication may be injected by means of a hypodermic needle. As is conventional, tubing 13 incorporates a drip rate indicator and regulator valve assembly, as generally indicated at 15, for regulating the flow of the I.V. solution from the bag to the patient further. Tubing 13 is typically connected to an I.V. catheter (not shown) inserted in a vein of a patient's forearm. Thus described, the bag 1, as above described, is conventional and well-known to those in the medical arts.

Further, as the I.V. solution drains from the bag, the liquid level L (see FIG. 2) of the I.V. solution in the bag will drop and the remaining I.V. solution will accumulate toward the bottom of the bag. As best shown in FIG. 2, the bag when full, its sidewalls 3a, 3b are spaced relatively far apart, as indicated by dimension X in FIG. 2, and as the I.V. solution is discharged from the bag, atmospheric pressure tends to collapse the bag (i.e., move the sidewalls 3a, 3b into close proximity with one another) above the liquid level L while still maintaining the bag in substantially its spaced apart or full condition, as indicated by dimension X.

As indicated generally by reference character 17, monitoring apparatus of the present invention is shown to be removably applied (resiliently clamped or clipped) to the exterior of I.V. bag 1 for indicating or monitoring when the liquid level L of the I.V. solution in the bag has drained down to a predetermined level, as is generally indicated by the position of the monitoring apparatus on the bag. As is used in the context of this invention, the term "monitor" is herein defined to mean generating an alarm or signal in response to the liquid level L of the I.V. solution in the bag reaching a predetermined position within the bag.

Apparatus 17 is shown to comprise a frame 19 having frame parts 21a and 21b spaced apart from one another and joined by a base 23 at one end thereof. Base 23 and frame arms 21a, 21b are shown to be of one-piece construction of a suitable synthetic resin material. Preferably, this resin material is sufficiently resilient so that it has a normally closed position (as shown in solid lines in FIG. 4) in which the frame arms 21a, 21b are spaced relatively close together. By forcing the arms 21i a, 21b apart from one another (as indicated in phantom in FIG. 4), the arms may be resiliently opened and frame 19 may be applied to the exterior of an I.V. bag 1 in the manner shown in FIGS. 1-3 with frame arm 21a located on the exterior of bag sidewall 3a and with frame arm 21b located on the exterior of bag wall 3b. Because of the resilient or springy construction of frame 19, the frame arms 21a, 21b will resiliently grip and be frictionally maintained in engagement with the bag sidewalls at a desired position (height) thereon, even as the spacing of the bag sidewalls decreases from their full dimension X, as shown in FIG. 2, to their collapsed position, as shown by dimension Y in FIG. 3.

Further in accordance with this invention, monitoring device 17 incorporates a signal generating circuit or means, as generally indicated at 25 in FIG. 6. This signal generating means includes a sensing device, as indicated at 27, and an actuator 29. As best shown in FIG. 5, sensing device 27 is carried by one frame arm, for example, arm 21a, and the actuating device 29 is carried by the other frame arm 23a so that the actuating device and the sensing device are located on opposite sides of bag 1. Signal generating means 25 further includes a power supply or battery, as indicated at 31, and a signaling means S. As shown in FIG. 6, this signaling means may include an aural alarm 33 (e.g., a horn or buzzer) or an indicator lamp 35. In addition, it will be understood that the signal alarm may also include a jack (not shown) into which suitable wiring (also not shown) may be plugged so as to interconnect the signal generating means 25 to a remote monitor located, for example, at a central nursing station, or connected to suitable circuitry to energize a lamp outside the door of the patient's hospital room. It will be understood that the contruction of the signal generating means shown in FIG. 6 is illustrative and those skilled in the art will recognize that circuits of many designs may be utilized in accordance with the present invention.

Preferably, signal generating means 25 is incorporated in and is carried by frame 19 so that the I.V. monitoring system is a self-contained unit carrying its own power supply and is capable of sounding its own alarm so as to make either the patient or nearby nursing personnel cognizant of the fact that the liquid level L of the I.V. solution in the I.V. bag 1 has been drained down to a predetermined level.

As shown in FIG. 6, sensing element 27 is preferably a magnetic reed switch carried within frame arm 21a on one side of bag 1 and the actuating element 29 is shown to be a permanent magnet imbedded in the other frame arm 21b on the opposite side of the bag. Thus, the magnetic reed switch and the magnet constitutes a proximity switch. Of course, magnet 29 generates lines of magnetic flux. With the monitoring device 17 applied to the exterior of the I.V. bag 1, as shown in FIG. 2, and with the frame arms 21a and 21b spaced relatively far apart from one another in their open position (shown in phantom lines in FIG. 4) and spaced from one another by the distance X when the bag is full, the magnetic flux generated by the magnet is not sufficient to close magnetic reed switch 27. As noted earlier, as the I.V. solution drains from the bag, the liquid level L of the I.V. solution will drop within the bag and the sidewalls of the bag above the liquid level will move toward one another until they are in close proximity relation (i.e., actually touching one another) as the result of atmospheric air pressure collapsing the bag. However, the lower portion of the bag containing the remainder of the I.V. solution will be maintained approximately in the position shown in FIG. 2 with the sidewalls of the bag still spaced relatively far apart from one another thereby preventing closing of the magnetic reed switch by the magnet. As the liquid level continues to drop in the bag and as the liquid level comes down to the approximate elevation of the location of the monitoring device 17 on the bag, the resilient frame arms 21a, 21b will move toward one another. As the arms move closer to one another, the magnetic flux of magnet 29 will pass through the walls of the bag and the I.V. solution and will trip (close) magnetic reed switch 27 thus sounding either an aural alarm via horn 33, light up indicator lamp 35, or send a signal to a remote monitoring station. This signal indicates that the liquid level L of the I.V. solution remaining in the bag has dropped down to a predetermined level, as generally indicated by the position of the monitoring device 17 on the bag.

Generally, I.V. bag 1 is provided with graduation markings G on the exterior of the bag indicating the approximate volume of the I.V. solution remaining in the bag. By comparing the liquid level L relative to the graduation markings G, hospital personnel may readily determine the approximate volume of the I.V. solution remaining in the bag. Further in accordance with the invention, frame 19 is provided with viewing windows 39 proximate the position of magnet 29 and magnetic reed switch 27 so that when graduation markings G are viewable through windows 39, the signal generating means 25 will be actuated when the liquid level drops approximately to the level of the graduation markings viewable through the windows 39. In this manner, it will be understood that by placing the frame 19 at any desired position along the height of bag 1, an alarm will be sounded when the liquid level has dropped within the bag to the approximate level of frame 19.

In use, the patient is fitted with the I.V. bag and catheter in the well-established and well-known manner. If, for example, an I.V. saline solutin is to be administered to the patient for a considerable length of time, the monitoring device 17 of this invention may be placed at the graduation markings G at the lower portion of the bag so that the alarm will be sounded when only a small fraction of the I.V. solution remains in the bag. Thus, since it may take many hours for the I.V. solution to be administered to the patient, nurses will not be required to keep a more or less constant check on the quantity of fluid remaining in the bag because as the liquid level drops to the approximate position of the monitor, the alarm will sound thus giving nursing personnel ample warning that the quantity of I.V. solution remaining in the bag is low but is not yet completely empty. In this manner, the bag may be changed before it runs dry, but without wasting appreciable quantities of the I.V. solution and without risking the consequences of permitting the I.V. bag to run dry.

Another use for the monitoring apparatus of the present invention may be that the treating physician would prescribe administering, for example, 500 cc. of a prescribed I.V. solution to a patient and after this quantity of solution has been administered, to inject a medication into the remaining I.V. solution. Monitoring apparatus 17 of the present invention may be positioned on the exterior of I.V. bag 1 with the graduation markings G of the bag indicating the first desired quantity of I.V. fluid to be administered to the patient being viewable through windows 39. Thus, after the first desired amount of I.V. solution has been administered, the signal generating means 25 will be actuated and the nurse can then administer the prescribed medication into the remaining I.V. solution.

Still further, it will be recognized that in the event the catheter or tubing becomes dislodged from the patient thus resulting in a rapid depletion of the I.V. solution in the bag, the signal generating means 25 of the present invention will be actuated thus alerting the nurses to the fact that the I.V. bag is in need of replacement.

Referring now to FIGS. 7 and 8, a second embodiment of the monitoring apparatus of the present invention is shown in its entirety by reference character 17'. Generally, the second embodiment of the monitoring apparatus 17' is similar in operation and function to monitoring apparatus 17 described above. Corresponding "primed" reference characters indicate parts having a similar function to parts bearing the same reference characters in regard to the first-mentioned embodiment.

Specifically, monitoring apparatus 17' includes a frame 19' having two frame arms 21a' and 21b' which are hingedly connected together at a hinge point, as indicated at 41. Frame arm 21a is shown to carry the sensing element 27' (also preferably a magnetic reed switch or other proximity switch) together with a aural horn 33' and a battery 31' enclosed in a battery container 37'. Frame arm 21b' includes actuating element 29' (preferably a permanent magnet for actuating the magnetic reed switch) opposite the location of the sensing element 27'. A hairpin spring 43 or the like is interposed between the handle portions 44a, 44b and extends outwardly from hinge point 41 and resiliently bears against handle portions 44a, 44b to bias the frame arms toward their closed position. It will be understood that by squeezing handle portions 44a, 44b toward one another, the biasing force of spring 43 may be overcome and the jaws or frame parts 21a' 21b' may be swung open to their open position for application of the monitoring apparatus to the exterior of a full I.V. bag 1 in the manner similar to apparatus 17 disclosed hereabove. Upon releasing the handle portions 44i a, 44b, spring 43 resiliently maintains the frame halves in gripping engagement with the bag.

The inner faces of jaws of frame members 21a', 21b' are provided with gripping teeth T or other suitable means so as to positively hold the monitoring apparatus 17 in its desired position on the exterior of bag 1. Further, handle portion 44a is shown to include a latch post 45 having a tab 47 extending therefrom. Handle portion 44b is shown to have an opening 49 therethrough for receiving the latch 45 whereby the frame parts 21a', 21b' may be positively locked and held in their open position to aid in the placement of the monitoring apparatus on the exterior of the bag without having to continuously apply force to overcome the bias of spring 43. Once the monitoring apparatus 17' is applied to the bag in a desired position, the latch may be released thereby allowing spring 43 to apply a resilient gripping pressure on the frame jaws so as to maintain the apparatus in its desired position on the bag.

Still further, as particularly illustrated in FIG. 8, the frame halves may be provided with lightening holes 51 so as to reduce the weight of and the material required for manufacture of frame 19. These holes may also be utilized to position the monitoring apparatus 17' proximate to bag graduation markings G in the manner above described in regard to apparatus 17 and its corresponding viewing windows 39.

Further in accordance with this invention, the method of the instant invention involves applying the monitoring device 17 or 17' to the exterior of a full I.V. bag 1 at a desired elevation or location thereon. Upon the I.V. solution being discharged from the bag and upon the liquid level L of the I.V. solution in the bag dropping down to a predetermined level proximate the location of the monitoring apparatus on the bag, the frame portions 21a and 21b will move toward one another from an open position toward a closed position which results in the actuation of signal generating means 25 thereby to generate a signal indicating that the liquid level L of the I.V. solution in the bag has dropped down to a predetermined level.

It will be appreciated that because the signal generating means 25 of the present invention is battery powered, all substanial risk of electrical shock to the patient or to hospital personnel is eliminated. It will further be appreciated that the monitoring apparatus of the present invention may be readily applied by hospital personnel to any I.V. bag containing any I.V. solution and of any size in a matter of seconds and may be readjusted as required.

In FIG. 9, still another embodiment of the sensing or monitoring device of this invention is indicated in its entirety by reference character 17″. This embodiment is similar in construction and operation to device 17 heretofore described and shown in FIGS. 1-6, except that the frame members 21a″, 21b″0 are substantially wider than frame members 21a, 21b. Additionally, frame members 21a″, 21b″ are each provided with an aperture A so as to accommodate hub H of bag 1 when the device is positioned low on the bag.

In view of the above, it will be seen that the objects of this invention are achieved and other advantages results obtained.

As various changes could be made in the above constructions or method without departing from the scope of the present invention, it is intended that all matter contained in the above description or shown in the accompanying drawings shall be interpreted as illustrative and not in a limiting sense.

What is claimed is:

1. Apparatus for monitoring the administering of an intravenous fluid or the like to a patient from a flexible wall container and for generating a signal upon the fluid in the container reaching a predetermined level, said container having an outlet for the fluid and flexible sidewalls which are spaced apart when said container is full and which move toward one another as said fluid is discharged, said apparatus comprising a frame having at least one resiliently movable portion adapted to be removably applied to the exterior of said container at any preselected location thereon, said frame being movable with said sidewalls, means carried by said frame for generating a signal in response to the fluid remaining in the container reaching said predetermined level, said signal generating means being movable with said at least one frame portion as the fluid is discharged from said container and as the container sidewalls move toward one another from an open position in which said signal generating means is de-energized to a closed position in which said signal generating means is actuated thereby to generate said signal indicating that the fluid remaining in the container has been reduced to said predetermined level.

2. Apparatus as set forth in claim 1 wherein said signal generating means includes a switch, the latter including an actuator carried by a first portion of said frame on one side of said container and a sensing element carried by another portion of said frame on the other side of said container, one of the last-said frame portions constituting said at least one movable frame portion, said switch energizing said signal generating means upon said sensing element and said actuator moving toward one another beyond a predetermined spacing therebetween as occasioned by said sidewalls of said container moving toward one another upon said fluid being discharged from said container.

3. Apparatus as set forth in claim 2 wherein said sensing element is a magnetic reed switch and wherein said actuator is a magnet.

4. Apparatus as set forth in claim 2 wherein said signal generator comprises a power supply and warning means operable by said power supply upon actuation of said switch.

5. Apparatus as set forth in claim 4 wherein said power supply is a battery carried by said frame.

6. Apparatus as set forth in claim 4 wherein said warning means is an aural alarm.

7. Apparatus as set forth in claim 4 wherein said warning means is a light.

8. Apparatus as set forth in claim 2 wherein said signal generating means further comprises means for transmitting said signal to a remote monitoring station.

9. Apparatus as set forth in claim 1 wherein said container comprises a collapsible bag made of pliable sheet material, said bag including graduation markings thereon indicating the approximate volume of fluid remaining in the bag when the latter is held in its normal discharging position, said frame including means thereon for permitting positioning of said frame relative to a selected said graduation markings on said bag so that said signal will be generated upon the level of the fluid in the bag being lowered approximately to the level of said selected graduation marking.

10. Apparatus for monitoring the administering of an intravenous fluid or the like to a patient from a flexible wall container and for generating a signal upon the fluid in the container reaching a predetermined level, said container having an outlet for the fluid and flexible sidewalls which are spaced apart when said container is full and which move toward one another as said fluid is discharged, said apparatus comprising a frame adapted to be removably applied to the exterior of said container at a preselected location thereon, said frame being movable with said sidewalls, means carried by said frame for generating a signal in response to the fluid remaining in the container reaching said predetermined level, said signal generating means being movable with the frame as the fluid is discharged from said container and as the container sidewalls move toward one another from an open position in which said signal generating means is de-energized to a closed position in which said signal generating means is actuated thereby to generate said signal indicating that the fluid remaining in the container has been reduced to said predetermined level, said frame including spring means for resiliently maintaining said frame in its desired position on said container as said fluid is discharged therefrom and as said container sidewalls move toward one another.

11. Apparatus as set forth in claim 10 further including means on said frame for enhancing gripping of the frame on said container.

12. A portable device removably appliable to a flexible wall bag containing a supply of liquid for intravenous administration to a patient, said device being capable of generating a signal in response to the level of the liquid inside said bag being lowered below a predetermined level, said bag having sidewalls of pliable sheet material and being adapted to be supported in a generally vertical position while dispensing the liquid therefrom with the sidewalls being generally vertical, said bag having an outlet at its lower end, said sidewalls being spaced apart when said bag is full of liquid and, as said liquid is dispensed via said outlet, the level of the liquid within the bag falling within the bag thus permitting the walls of the bag above the liquid level to move toward one another, said walls above the liquid level within the bag being in close proximity to one another and said walls below the liquid level being spaced relatively far apart, said device further comprising a resilient frame including a pair of arms, said arms being movable toward and away from one another between an open position and a closed position, said arms, being resiliently biased toward their closed position and, when in their open position, being capable of being applied to said bag full of said liquid with one arm on the outside of one sidewall of the bag and with the other arm on the outside of the other sidewall of the bag, said frame including signal generating means actuable upon said frame arms being movable from their open toward their closed positions as said side arms move with said bag walls thereby to indicate that the level of the liquid within the bag has fallen to approximately the location of said arms relative to the bag.

13. A method of monitoring the level of an intravenous liquid solution to be administered intravenously to a patient, said intravenous solution being contained in a flexible wall bag and being discharged from the bottom of the bag, wherein the steps of said method consist of;

supporting the bag in such fashion that a discharge outlet of the bag is at its bottom and the outlet is connected to the patient for the intravenous administration of said liquid contained in the bag;

applying a device to said bag at a desired location relative to the height of the bag, said device having a first portion thereof on the outside of one sidewall and another portion thereof on the outside of the other sidewall of the bag;

discharging said intravenous solution from the bag to the patient thereby causing the level of the solution to fall within the bag and causing the sidewalls of the bag above the level of the solution together with portions of said device to move toward one another; and generating a signal in response to the level of the intravenous solution in the bag falling below a predetermined point relative to the bag as occasioned by the portions of said device being moved toward one another.

* * * * *